United States Patent
Nielsen et al.

(10) Patent No.: US 10,561,335 B2
(45) Date of Patent: Feb. 18, 2020

(54) HEARING DEVICE COMPRISING ELECTRODES FOR PICKING UP A PHYSIOLOGICAL RESPONSE

(71) Applicants: Oticon A/S, Smørum (DK); Oticon Medical A/S, Smørum (DK)

(72) Inventors: Claus Nielsen, Smørum (DK); Thomas Lunner, Smørum (DK); Regin Kopp Pedersen, Smørum (DK); Carina Graversen, Smørum (DK); Dorothea Wendt, Smørum (DK); Karsten Bo Rasmussen, Smørum (DK); Eline Borch Petersen, Smørum (DK); Troels Holm Pedersen, Smørum (DK); Martin Lindebjerg, Smørum (DK)

(73) Assignee: Oticon A/S, Smørum (DK)

( * ) Notice: Subject to any disclaimer, the term of this patent is extended or adjusted under 35 U.S.C. 154(b) by 242 days.

(21) Appl. No.: 15/497,775

(22) Filed: Apr. 26, 2017

(65) Prior Publication Data

US 2017/0311097 A1 Oct. 26, 2017

(30) Foreign Application Priority Data

Apr. 26, 2016 (EP) .................................... 16167045

(51) Int. Cl.
*H04R 25/00* (2006.01)
*A61B 5/00* (2006.01)
(Continued)

(52) U.S. Cl.
CPC .......... *A61B 5/0484* (2013.01); *A61B 5/0496* (2013.01); *A61B 5/4094* (2013.01);
(Continued)

(58) Field of Classification Search
CPC . A61B 5/0484; A61B 5/04001; A61B 5/4094; A61B 5/0496; A61B 5/6817;
(Continued)

(56) References Cited

U.S. PATENT DOCUMENTS

2003/0195588 A1  10/2003  Fischell et al.
2004/0220644 A1  11/2004  Shalev et al.
(Continued)

FOREIGN PATENT DOCUMENTS

EP   2 200 347 B1   1/2013
EP   2 826 521 A1   1/2015
(Continued)

OTHER PUBLICATIONS

Petersen et al., "Generic Single-Channel Detection of Absence Seizures," 33rd Annual International Conference of the IEEE EMBS, Boston, Massachusetts, USA, Aug. 30-Sep. 3, 2011, pp. 4820-4823.

*Primary Examiner* — Mark Bockelman
(74) *Attorney, Agent, or Firm* — Birch, Stewart, Kolasch & Birch, LLP

(57) ABSTRACT

The application relates to a hearing device, e.g. a hearing aid, comprising a first part for being inserted in an ear canal or fully or partially implanted in the head of a user, the first part comprising at least one electrode unit, termed a PR-electrode unit, for making contact to skin or tissue of a user when mounted or implanted in an operational condition, the at least one PR-electrode unit being configured to pick up a physiological response from the user, and wherein the at least one PR-electrode unit comprises an electrically conductive material, e.g. a shape memory alloy. The first part may comprise an implanted part, e.g. in combination with an external part adapted for being located in an ear canal, wherein both parts comprise one or more PR-electrode units. The invention may e.g. be used hearing aids, headsets, ear phones, active ear protection systems, or combinations
(Continued)

thereof, e.g. to control processing of the hearing device or to monitor a condition of the user wearing the hearing device.

19 Claims, 10 Drawing Sheets

(51) Int. Cl.
    *A61B 5/0484*     (2006.01)
    *A61B 5/0496*     (2006.01)

(52) U.S. Cl.
    CPC .......... *A61B 5/6817* (2013.01); *H04R 25/505* (2013.01); *H04R 25/554* (2013.01); *H04R 2225/025* (2013.01); *H04R 2225/55* (2013.01); *H04R 2225/67* (2013.01)

(58) Field of Classification Search
    CPC ........ A61B 2560/0468; A61N 1/36036; A61N 1/0541; H04R 25/652; H04R 25/604; H04R 25/552; H04R 2225/67; H04R 2225/025; H04R 25/554; H04R 25/505; H04R 2225/55
See application file for complete search history.

(56) References Cited

U.S. PATENT DOCUMENTS

| | | |
|---|---|---|
| 2006/0094974 A1 | 5/2006 | Cain |
| 2010/0191305 A1 | 7/2010 | Imran et al. |
| 2010/0196861 A1 | 8/2010 | Lunner |
| 2012/0238856 A1 | 9/2012 | Kidmose et al. |
| 2015/0360030 A1 | 12/2015 | Cartledge et al. |

FOREIGN PATENT DOCUMENTS

| | | |
|---|---|---|
| EP | 2 986 031 A1 | 2/2016 |
| EP | 2 997 893 A1 | 3/2016 |

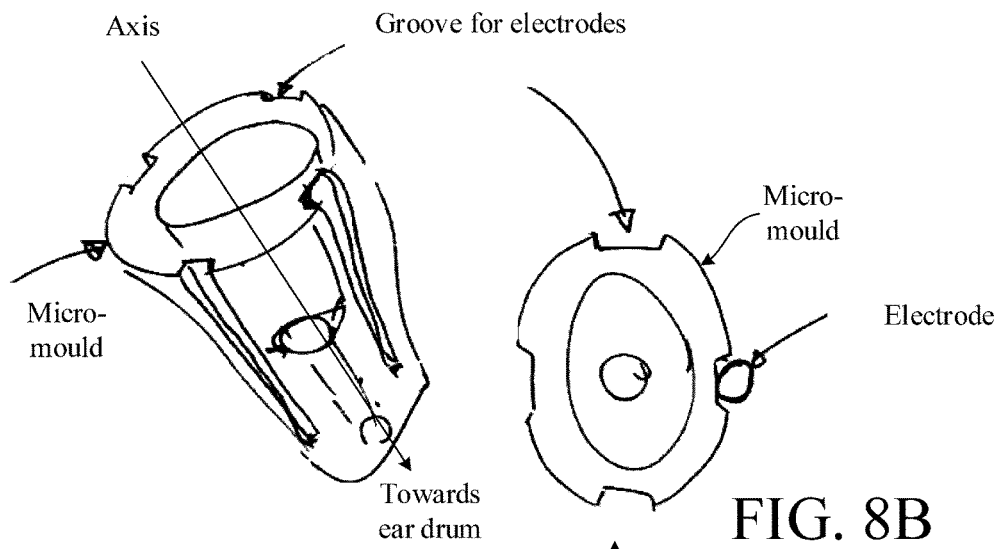
FIG. 8A
FIG. 8B
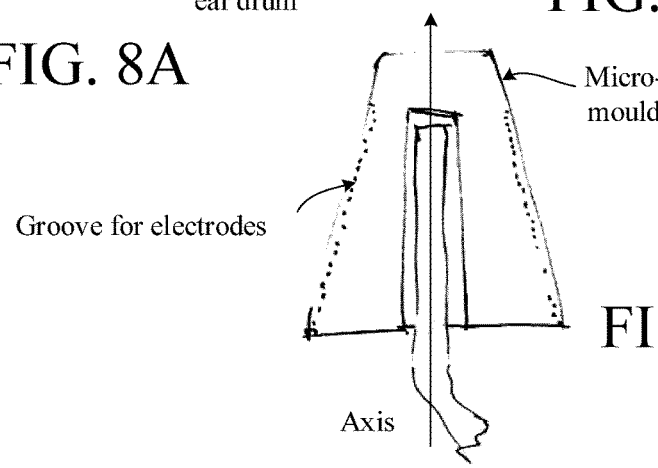
FIG. 8C

HEARING DEVICE COMPRISING ELECTRODES FOR PICKING UP A PHYSIOLOGICAL RESPONSE

SUMMARY

The present application relates to the field of hearing devices, e.g. hearing aids.

One type of hearing devices is air conduction hearing aids having one or more external parts adapted to be located at or in an ear (e.g. in an ear canal) of a user and comprising an output transducer for delivering an acoustic signal to an ear drum of a user's ear. In an embodiment, the hearing aid comprises a first part adapted for being located at an ear or in an ear canal of the user. The first part may comprise one or more electrodes for picking up (electro) physiological responses, e.g. brainwave signals, cf. e.g. US20100196861A1.

Another type of hearing devices are implantable hearing aids, e.g. hearing aids comprising one or more implanted parts, e.g. a cochlear implant comprising an electrode array. Measurement of physiological responses to stimuli presented by implanted devices may be used to evaluate the functionality of implants, e.g. to detect response thresholds and as a guide towards optimal stimulus intensity settings. Monitoring of (electro) physiological responses often requires advanced dedicated equipment and complex and/or time consuming test setups. Monitoring of e.g. ABR (auditory brainstem response) and EEG (electroencephalography) involves placement of a number of external electrodes on the skin of the patient head, or e.g. in an ear canal, connected to an (possibly external) amplifier. At least for some electrodes, good electrical contact should preferably be established between each electrode and the skin or tissue of the user. In the case of a cochlear or brain stem implant, an electrode array is inserted into the cochlear or on the brain stem to provide auditory sensation. The stimuli are e.g. generated by an implanted device placed in a pocket underneath the skin on the scull. The implanted device incorporates an antenna (typically using magnetic induction) to communicate with an external sound processor or fitting system. Current devices incorporate means of monitoring electrophysiological responses using the inserted electrode array plus in some cases a reference electrode placed on the electrode array itself or a separate electrode lead (see e.g. EP2826521A1). Today's equipment does not allow quality pickup of ABR or EEG signals directly by standard implants. Adding a number of electrode contact points on the implant itself, the part that contains the electronics and/or antenna, on the surface facing the skull will allow picking up electro physiological responses such as EEG (electroencephalography) or EOG (electrooculography) or ECoG (electrocorticography) directly by the implant electronics and transmission of the signals to an external system (such as an external processor or a fitting interface and software) through the built in antenna, or to process the responses in a processor of the implanted device. Use of multiple implants with surface electrodes (e.g. bilateral implants) will allow more information to be collected and may potentially allow pickup of and localisation of more distant responses (closer to the auditory cortex of the brain). The cochlear implant hearing device may comprise a processor for analysing the physiological responses, and e.g. be configured to influence or control the stimulation of the hearing nerve by the electrode array based on such analysis. In an embodiment, an electrooculogram (EOG) for monitoring eye movements of the user may be recorded by one or more electrodes located on a housing of an implanted part or by one or more separate implanted electrodes (preferably two electrodes (e.g. one to the left and one to the right of an eye) at each side of the head to monitor the movements of both eyes).

A combination of physiological responses (e.g. EEG and/or EOG) picked up by electrodes on an external ITE-part located in an ear canal and by electrodes located on an implanted part or separate implanted electrodes is furthermore proposed. The combination of responses may e.g. be used to control processing of the implant (and/or an external device, e.g. an air conduction or bone conduction hearing aid). In an embodiment, the hearing device comprises an electro-acoustic transducer for acoustically stimulating a first frequency range and an electrode array for electrically stimulating a second frequency range. In an embodiment, the combination of physiological responses may be used to define the distribution of frequency ranges stimulated by the acoustic transducer and the electrode array, respectively.

A Hearing Device:

In an aspect of the present application, a hearing device comprising a first part for being inserted in an ear canal or fully or partially implanted in the head of a user, the first part comprising at least one electrode unit, termed a PR-electrode unit, for making contact to skin or tissue of a user when mounted or implanted in an operational condition, the at least one PR-electrode unit being configured to pick up a physiological response from the user is provided. The hearing device further provides that the at least one PR-electrode unit comprises an electrode comprising an electrically conductive material.

Thereby an improved hearing device may be provided.

In an embodiment, the physiological response (PR) is represented by an evoked electric potential, e.g. an optically, electrically or acoustically evoked potential. In an embodiment, the PR-electrode unit is configured to pick up evoked potentials from the brain, e.g. using EEG (electroencephalography), or ECoG (electrocorticography), or from the eyes, e.g. EOG (electrooculography). In an embodiment, the PR-electrode unit comprises an electrical potential and/or magnetic field sensor configured to sense electric and/or magnetic brain wave signals, respectively. In an embodiment, an electrode of the PR-electrode unit is configured to be capacitively or inductively coupled to the head of a user of the hearing aid, when the hearing device is operatively mounted on the user. In an embodiment, an electrode of the PR-electrode unit comprises an inductor, e.g. a coil. In an embodiment, an electrode of the PR-electrode unit comprises a capacitor, e.g. a patch.

Some electrodes for electrophysiological measurements like EEG measurements need to have good contact with the skin. Traditional measurement electrodes are often used with electrode paste to ensure good electrical contact. If the electrodes are to be placed in the outer ear or ear canal for ear EEG measurements, electrodes will typically be placed in the mould or shell of the hearing aid. In order to achieve good skin contact the electrodes typically protrude out of the mould/shell surface (see e.g. FIG. 1A). This protrusion is problematic both during insertion of the earpiece (scraping the skin) and whilst sitting in the ear because the ear canal is sensitive to pressure. The same aim and problems are encountered for implanted electrodes for monitoring physiological responses, such electrodes being e.g. located on a housing shell of an implanted part.

The present inventors propose to use electrodes mounted in the surface of an ear piece (e.g. an ear mould or shell), or of an implanted part of a hearing aid, made of memory metal (memory alloy). An electrode is e.g. adapted to—whilst it is outside the ear (or not yet implanted)—have a shape flush with the surface of the ear mould/shell, and—once it is placed in the ear canal (or fully or partially implanted in the head) of a user and heated up to body temperature—to change shape and protrude from the surface. The protrusion is preferably adapted to make good contact with the skin.

This idea will solve the problem of insertion of an earpiece or implanted part with protruding electrodes that may scrape the skin (externally when inserted in an ear canal, or internally when implanted under the skin). An ear piece with electrodes according to the present disclosure can potentially be made to provide comfort during use of the hearing aid.

In an embodiment, the hearing device comprises a housing (and/or a guiding element), and the at least one PR-electrode unit comprises a PR-electrode that is adapted to have an outer surface that is flush with or depressed in the surface of the housing of the first part at temperatures below a threshold temperature, and to protrude from the surface when heated to temperatures at or above said threshold temperature. In an embodiment, 'a housing' may include a shell for enclosing components of the hearing aid), a possibly customized ear mould. In an embodiment, 'a guiding element' may include a micro mould or a dome-like structure (e.g. of a flexible material).

In an embodiment, the protrusion of the PR-electrode from the outer surface of the housing is adapted to make good contact with the skin at and above said threshold temperature.

In an embodiment, the PR-electrode unit comprises an element of a material that expands its volume when heated from below the threshold temperature to above the threshold temperature. In an embodiment, the element shrinks its volume when cooled from above the threshold temperature to below the threshold temperature. In an embodiment, the material and the element is selected or adapted to provide that the expansion of the element and the resulting protrusion of the PR-electrode from the outer surface of the first part provides a good contact between with the PR-electrode and the skin or tissue of the user when mounted or implanted. In an embodiment, the volume change of the element is predominantly in a direction perpendicular to the surface of the PR-electrode that is in contact with the skin or tissue when the first part is mounted or implanted. In an embodiment, the element form part of the PR-electrode. In an embodiment, the element is located in the PR-electrode unit adjacent to the PR-electrode.

In an embodiment, the PR-electrode unit comprises a shape-memory material. In an embodiment, the electrically conductive material comprises a shape memory material. e.g. a shape memory alloy.

In an embodiment, the hearing device is configured to provide that said threshold temperature is below a normal body temperature of a human being. In an embodiment, the hearing device is configured to provide that said threshold temperature is below 37° C. e.g. below 35° C. In an embodiment, the hearing device is configured to provide that said threshold temperature is in the range from 32° C. to 40° C., such as in the range from 35° C. to 38° C.

In an embodiment, the first part comprises a part for being inserted in an ear canal of the user.

In an embodiment, the first part comprises a part for being fully or partially implanted in the head of the user.

In an embodiment, the hearing device comprises a reference electrode. In an embodiment, the hearing device comprises a separate reference electrode implanted in the head of the user. In an embodiment, the reference electrode is located in or on the first part. In an embodiment, the hearing device comprises a separate PR-electrode implanted in the head of the user (separate from possible PR-electrodes on the housing of the implanted part).

In an embodiment, the hearing device comprises a processor for analysing the physiological responses from the PR-electrode units, and configured to influence or control the stimulation of the hearing nerve by the electrode array based such analysis. In an embodiment, the hearing device comprises an electrode array for electrically stimulating a hearing nerve of the user, and a processor for analysing the physiological responses from the PR-electrode units, and configured to influence or control the stimulation of the hearing nerve based on such analysis.

In an embodiment, the hearing device comprises an external ITE-part located at or in an ear canal and an implanted part, each part comprising one or more PR-electrode units, the hearing device being configured to combine physiological responses picked up said PR-electrode units. In an embodiment, the hearing device comprises an ITE-part as well as an implanted part. In an embodiment, only one of the ITE-part and the implanted part (e.g. the implanted part or the ITE-part) comprises one or more PR-electrodes.

In an embodiment, the hearing device comprises an electro-acoustic transducer for acoustically stimulating a first frequency range and wherein said implanted part comprises an electrode array for electrically stimulating a second frequency range.

In an embodiment, the hearing device is configured to use the physiological responses from said PR-electrode units in combination to control processing of the implanted part. In an embodiment, the hearing device is configured to use the combination of physiological responses to define the distribution of frequency ranges stimulated by the acoustic transducer and the electrode array, respectively.

In an embodiment, the hearing device is configured to record an electro oculogram (EOG) for monitoring eye movements of the user.

In an embodiment, the hearing device is configured to monitor epilepsy or epileptic seizures based on the physiological responses from said PR-electrode units.

In an embodiment, the hearing device comprises a hearing aid for compensating a user's hearing impairment.

In an embodiment, the hearing device is adapted to provide a frequency dependent gain and/or a level dependent compression and/or a transposition (with or without frequency compression) of one or frequency ranges to one or more other frequency ranges, e.g. to compensate for a hearing impairment of a user. In an embodiment, the hearing device comprises a signal processing unit for enhancing the input signals and providing a processed output signal.

In an embodiment, the hearing device comprises an output unit for providing a stimulus perceived by the user as an acoustic signal based on a processed electric signal. In an embodiment, the output unit comprises a number of electrodes of a cochlear implant or a vibrator of a bone conducting hearing device. In an embodiment, the output unit comprises an output transducer. In an embodiment, the output transducer comprises a receiver (loudspeaker) for providing the stimulus as an acoustic signal to the user. In an embodiment, the output transducer comprises a vibrator for providing the stimulus as mechanical vibration of a skull bone to the user (e.g. in a bone-attached or bone-anchored hearing device). In an embodiment, the hearing device comprises a multi-electrode array for electric stimulation in combination with a loudspeaker for acoustic stimulation and/or a vibrator for bone-conducted stimulation.

In an embodiment, the hearing device comprises an input unit for providing an electric input signal representing sound. In an embodiment, the input unit comprises an input transducer. e.g. a microphone, for converting an input sound to an electric input signal. In an embodiment, the input unit comprises a wireless receiver for receiving a wireless signal comprising sound and for providing an electric input signal representing said sound. In an embodiment, the hearing device comprises a directional microphone system adapted to spatially filter sounds from the environment, and thereby enhance a target acoustic source among a multitude of acoustic sources in the local environment of the user wearing the hearing device. In an embodiment, the directional system is adapted to detect (such as adaptively detect) from which direction a particular part of the microphone signal originates.

In an embodiment, the hearing device comprises an antenna and transceiver circuitry for wirelessly receiving a direct electric input signal from another device, e.g. a communication device or another hearing device. In an embodiment, the hearing device comprises a (possibly standardized) electric interface (e.g. in the form of a connector) for receiving a wired direct electric input signal from another device, e.g. a communication device or another hearing device. In an embodiment, the direct electric input signal represents or comprises an audio signal and/or a control signal and/or an information signal. In an embodiment, the hearing device comprises demodulation circuitry for demodulating the received direct electric input to provide the direct electric input signal representing an audio signal and/or a control signal e.g. for setting an operational parameter (e.g. volume) and/or a processing parameter of the hearing device. In general, a wireless link established by a transmitter and antenna and transceiver circuitry of the hearing device can be of any type. In an embodiment, the wireless link is used under power constraints, e.g. in that the hearing device comprises a portable (typically battery driven) device. In an embodiment, the wireless link is a link based on near-field communication, e.g. an inductive link based on an inductive coupling between antenna coils of transmitter and receiver parts. In another embodiment, the wireless link is based on far-field, electromagnetic radiation.

In an embodiment, communication between the hearing device and the other device is based on some sort of modulation at frequencies above 100 kHz. Preferably, frequencies used to establish a communication link between the hearing device and the other device is below 50 GHz, e.g. located in a range from 50 MHz to 50 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). In an embodiment, the wireless link is based on a standardized or proprietary technology. In an embodiment, the wireless link is based on Bluetooth technology (e.g. Bluetooth Low-Energy technology or technologies based thereon).

In an embodiment, the hearing device is portable device, e.g. a device comprising a local energy source, e.g. a battery, e.g. a rechargeable battery.

In an embodiment, the hearing device comprises a forward or signal path between an input transducer (microphone system and/or direct electric input (e.g. a wireless receiver)) and an output transducer. In an embodiment, the signal processing unit is located in the forward path. In an embodiment, the signal processing unit is adapted to provide a frequency dependent gain according to a user's particular needs. In an embodiment, the hearing device comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, an analogue electric signal representing an acoustic signal and/or a physiologic response, e.g. from the brain or an eye, e.g. an evoked potential, is converted to a digital audio signal in an analogue-to-digital (AD) conversion process (e.g. using a reference potential from a reference voltage, e.g. an external or implanted reference electrode), where the analogue signal is sampled with a predefined sampling frequency or rate $f_s$, $f_s$ being e.g. in the range from 0.5 kHz to 48 kHz (adapted to the particular signals or needs of the application) to provide digital samples $x_n$ (or x[n]) at discrete points in time $t_n$ (or n), each audio sample representing the value of the acoustic signal at $t_n$ by a predefined number $N_s$ of bits, $N_s$ being e.g. in the range from 1 to 16 bits. A digital sample x has a length in time of $1/f_s$, e.g. 50 µs, for $f_s$=20 kHz, or 1 ms, for $f_s$=1 kHz. In an embodiment, a number of audio samples are arranged in a time frame. In an embodiment, a time frame comprises 8, or 32, or 64, or 128 or more data samples. Other frame lengths may be used depending on the practical application.

In an embodiment, the hearing devices comprise an analogue-to-digital (AD) converter to digitize an analogue input with a predefined sampling rate. In an embodiment, the hearing device comprise a digital-to-analogue (DA) converter to convert a digital signal to an analogue output signal, e.g. for being presented to a user via an output transducer.

In an embodiment, the hearing device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the hearing device from a minimum frequency $f_{min}$ to a maximum frequency $f_{max}$ comprises a part of the typical human audible frequency range from 20 Hz to 20 kHz, e.g. a part of the range from 20 Hz to 12 kHz. In an embodiment, a signal of the forward and/or analysis path of the hearing device is split into a number NI of frequency bands, where NI is e.g. larger than 5, such as larger than 10, such as larger than 50, such as larger than 100, such as larger than 500, at least some of which are processed individually. In an embodiment, the hearing device is/are adapted to process a signal of the forward and/or analysis path in a number NP of different frequency channels (NP≤NI). The frequency channels may be uniform or non-uniform in width (e.g. increasing in width with frequency), overlapping or non-overlapping.

In an embodiment, the hearing device comprises a number of detectors configured to provide status signals relating to a current physical environment of the hearing device (e.g. the current acoustic environment), and/or to a current state of the user wearing the hearing device, and/or to a current state or mode of operation of the hearing device. Alternatively or additionally, one or more detectors may form part of an external device in communication (e.g. wirelessly) with the hearing device. An external device may e.g. comprise another hearing assistance device, a remote control, and audio delivery device, a telephone (e.g. a Smartphone), an external sensor, etc.

In an embodiment, one or more of the number of detectors operate(s) on the full band signal (time domain). In an embodiment, one or more of the number of detectors operate(s) on band split signals ((time-) frequency domain).

In an embodiment, the number of detectors comprises a level detector for estimating a current level of a signal of the forward path. In an embodiment, the predefined criterion comprises whether the current level of a signal of the forward path is above or below a given (L-) threshold value.

In a particular embodiment, the hearing device comprises a voice activity detector (VAD) for determining whether or not an input signal comprises a voice signal (e.g. comprising speech, at a given point in time). In an embodiment, the hearing device comprises an own voice detector for detecting whether a given input sound (e.g. a voice) originates from the voice of the user of the device or system.

In an embodiment, the hearing assistance device comprises a classification unit configured to classify the current situation based on input signals from (at least some of) the detectors, and possibly other inputs as well. In the present context 'a current situation' is taken to be defined by one or more of
a) the physical environment (e.g. including the current electromagnetic environment, e.g. the occurrence of electromagnetic signals (e.g. comprising audio and/or control signals) intended or not intended for reception by the hearing device, or other properties of the current environment than acoustic;
b) the current acoustic situation (input level, feedback, etc.), and
c) the current mode or state of the user (movement, temperature, etc.);
d) the current mode or state of the hearing assistance device (program selected, time elapsed since last user interaction, etc.) and/or of another device in communication with the hearing device.

In an embodiment, the hearing device further comprises other relevant functionality for the application in question, e.g. compression, noise reduction, feedback suppression, etc.

In an embodiment, the hearing device comprises a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof.

In a further aspect, of the present disclosure, grooves are formed into a micro-mould along a dimension which is parallel to an axis from ear canal entrance towards ear drum (when the micro-mould is mounted in the ear canal). These grooves allow for mounting of electrodes therein, e.g. made of electrically conducting material, such as metal, or conducting textile, or conducting rubber or polymer, etc. In an embodiment, such micro-mould form part of a hearing aid for being fully or partially inserted into an ear canal of a user.

In a further aspect, a soft dome or dome-like guiding element having electrodes applied thereon is provided. In an embodiment, such guiding element form part of a hearing aid for being fully or partially inserted into an ear canal of a user.

In an embodiment, (at least one of) the at least one PR-electrode is located on a housing or a mould or a guiding element of the first part. In an embodiment, the guiding element comprises a micro-mould or a dome.

In an embodiment, (at least one of) the at least one PR-electrode comprises an active electrode in the meaning that at least one of electrical amplification, impedance matching and analogue to digital conversion is performed in close proximity to the electrodes, e.g. in the first part.

In an embodiment, the first part comprises a housing or an ear mould or a guiding element, wherein one or more grooves are formed into the surface of the housing or ear mould or guiding element along a dimension which is parallel to an axis from ear canal entrance to ear drum when the first part is mounted in the ear canal.

Use:

In an aspect, use of a hearing device as described above, in the 'detailed description of embodiments' and in the claims, is moreover provided. In an embodiment, use is provided in a system comprising audio distribution. In an embodiment, use is provided in a system comprising one or more hearing instruments, headsets, ear phones, active ear protection systems, etc., e.g. in handsfree telephone systems, teleconferencing systems, public address systems, karaoke systems, classroom amplification systems, etc.

A Hearing System:

In a further aspect, a hearing system comprising a hearing device as described above, in the 'detailed description of embodiments', and in the claims, AND an auxiliary device is moreover provided.

In an embodiment, the system is adapted to establish a communication link between the hearing device and the auxiliary device to provide that information (e.g. control and status signals, possibly audio signals) can be exchanged or forwarded from one to the other.

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing device. In an embodiment, the auxiliary device is or comprises a remote control for controlling functionality and operation of the hearing device(s). In an embodiment, the function of a remote control is implemented in a SmartPhone, the SmartPhone possibly running an APP allowing to control the functionality of the audio processing device via the SmartPhone (the hearing device(s) comprising an appropriate wireless interface to the SmartPhone, e.g. based on Bluetooth or some other standardized or proprietary scheme).

In an embodiment, the auxiliary device is another hearing device. In an embodiment, the hearing system comprises two hearing devices adapted to implement a binaural hearing system, e.g. a binaural hearing aid system.

A Binaural Hearing System:

in a further aspect, a binaural hearing system comprising first and second hearing devices as described above, in the 'detailed description of embodiments', and in the claims, is moreover provided. The first and second hearing devices comprises circuitry for establishing a communication link between them to allow the transmission of audio and/or information signals from one to each other. In an embodiment, the binaural hearing system is configured to allow communication between the first and/or second hearing devices and a cell phone, e.g. a smartphone. In an embodiment, the binaural hearing system is configured provide that further processing of signals from PR-electrodes is performed in an external processing unit. e.g. in a smartphone.
Definitions:

In the present context, a 'hearing device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing device may comprise a single unit or several units communicating electronically with each other.

More generally, a hearing device comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit for processing the input audio signal and an output means for providing an audible signal to the user in dependence on the processed audio signal. In some hearing devices, an amplifier may constitute the signal processing circuit. The signal processing circuit typically comprises one or more (integrated or separate) memory elements for executing programs and/or for storing parameters used (or potentially used) in the processing and/or for storing information relevant for the function of the hearing device and/or for storing information (e.g. processed information, e.g. provided by the signal processing circuit), e.g. for use in connection with an interface to a user and/or an interface to a programming device. In some hearing devices, the output means may comprise an output transducer, such as e.g. a loudspeaker for providing an air-borne acoustic signal or a vibrator for providing a structure-borne or liquid-borne acoustic signal. In some hearing devices, the output means may comprise one or more output electrodes for providing electric signals.

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'hearing system' refers to a system comprising one or two hearing devices, and a 'binaural hearing system' refers to a system comprising two hearing devices and being adapted to cooperatively provide audible signals to both of the user's ears. Hearing systems or binaural hearing systems may further comprise one or more 'auxiliary devices', which communicate with the hearing device(s) and affect and/or benefit from the function of the hearing device(s). Auxiliary devices may be e.g. remote controls, audio gateway devices, mobile phones (e.g. SmartPhones), public-address systems, car audio systems or music players. Hearing devices, hearing systems or binaural hearing systems may e.g. be used for compensating for a hearing-impaired person's loss of hearing capability, augmenting or protecting a normal-hearing person's hearing capability and/or conveying electronic audio signals to a person.

Embodiments of the disclosure may e.g. be useful in applications such as hearing aids, headsets, ear phones, active ear protection systems, or combinations thereof.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 8A, 8B, 8C illustrate an embodiment of a micromould intended for insertion in an ear canal of a user and comprising grooves for locating a number of electrodes.

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

Figure 1A:
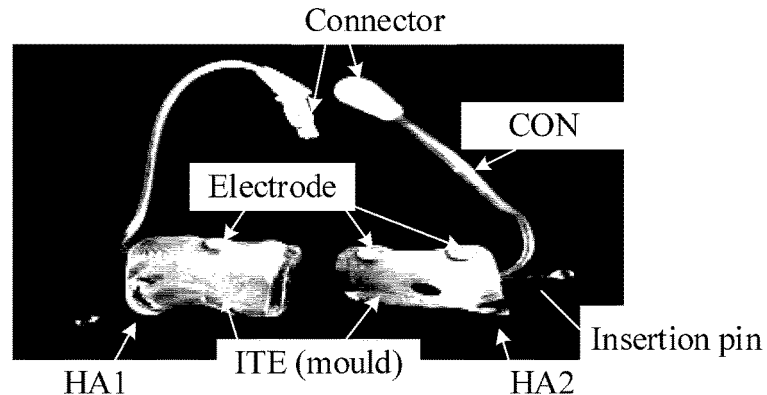
FIG. 1A shows an embodiment of a binaural hearing system comprising first and second hearing devices according to the present disclosure, FIG. 1B schematically illustrates an embodiment of a hearing device comprising an ITE-part adapted for being located in an ear canal of a user and comprising a PR-electrode unit according to the present disclosure for picking up a physiological response (PR) from the user.

FIG. 1A shows an embodiment of a binaural hearing system, e.g. a binaural hearing aid system, comprising first and second hearing devices (HA1, HA2). Each hearing aid comprises an ITE-part (ITE (mould)) adapted for being located in (and e.g. customized in form to) an ear canal of a (e.g. particular) user. Each ITE-part comprises a number of PR-electrode units (Electrode in FIG. 1A) adapted to pick up physiological responses (PR) from the user, e.g. spontaneous or evoked potentials, e.g. EEG or EOG-potentials. Each ITE-part comprises a connecting element (CON) with a connector (Connector) adapted to allow electronic parts of the ITE-part (e.g. the PR-electrode units) to be connected to another part of the hearing device, e.g. a BTE-part adapted to be located behind an ear of the user (cf. e.g. BTE in FIG. 6). The hearing devices of FIG. 1A may illustrate a current realization of an electrode in an ear EEG apparatus as a cylindrical (disk-shaped) element of an electrically conductive material, e.g. a metallic alloy, where the electrodes are adapted to protrude from the outer surface of the ITE-part to create a good electrical contact with the skin of the ear canal.

Figure 1B:
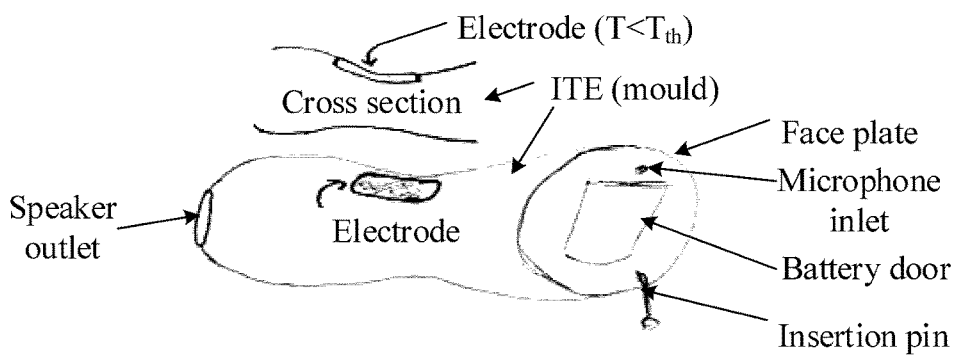
FIG. 1C illustrates an operational location of an ITE-part comprising a number of a PR-electrode units according to the present disclosure in the ear of a user, FIG. 2A schematically shows the insertion of an ITE-part of a hearing device comprising a number of a PR-electrode units according to the present disclosure in the ear of a user.

FIG. 1B schematically illustrates an embodiment of a hearing device comprising an ITE-part comprising an ear mould (ITE (mould)) adapted for being located in an ear canal of a user and comprising a PR-electrode unit (Electrode) according to the present disclosure. The ITE-part comprise a forward path comprising a microphone, a signal processing unit and a loudspeaker. As illustrated in the bottom part of FIG. 1B, the microphone inlet (Microphone inlet) is located in a Face plate allowing sound from the environment to be picked up by the microphone and converted to an electric input signal. The signal processing unit is configured to process (e.g. amplify or attenuate) the electric input signal according to a user's needs. The loudspeaker converts the processed signal to a sound for presentation to a user's ear drum via a Speaker outlet. The ITE-part further comprises a battery for energizing electronic components of the ITE-part (and a door for accessing the battery) and an insertion/removal element for insertion and/or removal of the ITE-part into/from the ear canal (cf. Battery door and Insertion pin, respectively, in the Face plate of the ITE-part). The top part of FIG. 1B illustrates a Cross section of an embodiment of an ITE-part comprising a PR-electrode unit comprising a PR-electrode having a surface that is flush with the outer surface of the ITE-part, when the temperature is below a threshold temperature ($T_{th}$), e.g. below a typical body temperature (as indicated in FIG. 1B by Electrode ($T<T_{th}$)), i.e. e.g. when the ITE-part is NOT located in contact with the body of a user). In the embodiment of FIG. 1B, the electrodes are shaped to follow the form of the (possibly customized) ear mould (ITE (mould)), and thus to follow the ear canal walls of the user when mounted.

Figure 1C:
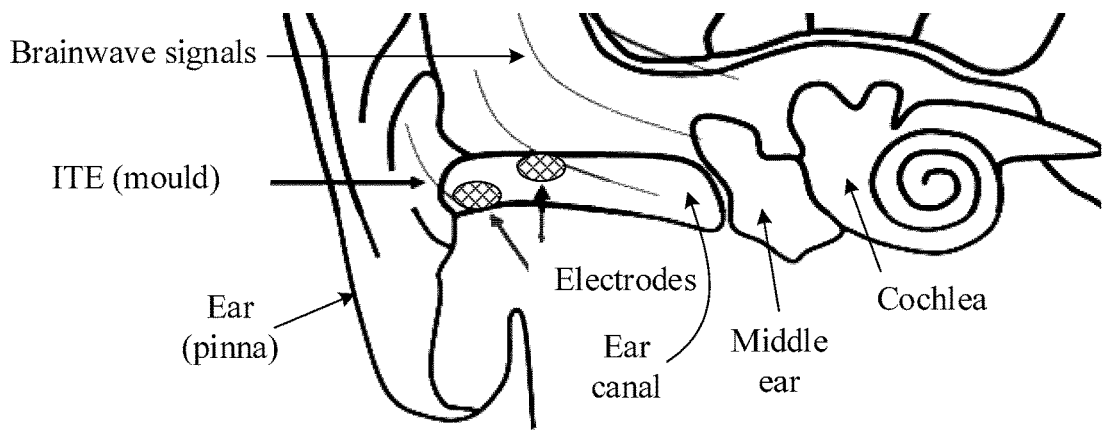

FIG. 1C illustrates an operational location of an ITE-part (ITE (mould)) comprising a number of PR-electrode units according to the present disclosure at the ear (Ear (pinna)), specifically in the Ear canal of a user. The PR-electrodes (Electrodes) of the PR-electrode units are in contact with the skin of the user in the ear canal and thus assume the temperature of the user's body. The electrodes are e.g. configured to pick up signals from the user's brain (Brainwave signals in FIG. 1C), e.g. EEG or EOG signals, e.g. to pick up spontaneous or evoked potentials. The Ear canal, the Middle ear and Cochlea are schematically shown in FIG. 1C.

The electrodes shown in FIGS. 1A, 1B and 1C can be of any type, e.g. of the dry or wet electrode type.

Figure 2A:
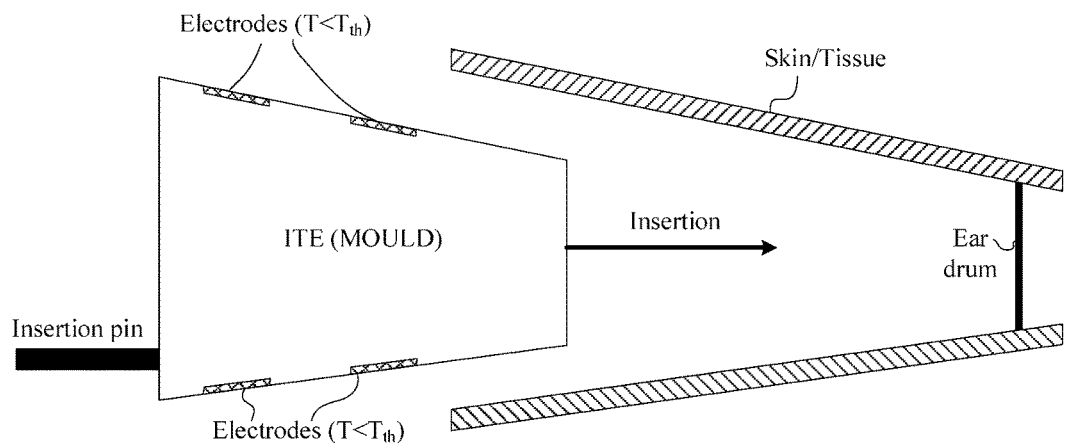
FIG. 2B illustrates the ITE-part of FIG. 2A when mounted in an operational location in the ear canal.

FIG. 2A schematically illustrates an ITE-part (ITE (mould)) of a hearing device according to the present disclosure, the ITE-part comprising a number of a PR-electrode units each comprising a PR-electrode (Electrodes ($T<T_{th}$)), during the process of the Insertion into an Ear canal towards the Ear drum of a user. The ITE-part comprises an Insertion pin for inserting and removing the ITE-part from the ear canal. While outside the ear canal (where the temperature is assumed to be smaller than a threshold temperature ($T<T_{th}$), e.g. smaller than a typical body temperature of a human being), the PR-electrodes are shown to be flush with the outer surface of the ITE-part.

Figure 2B:
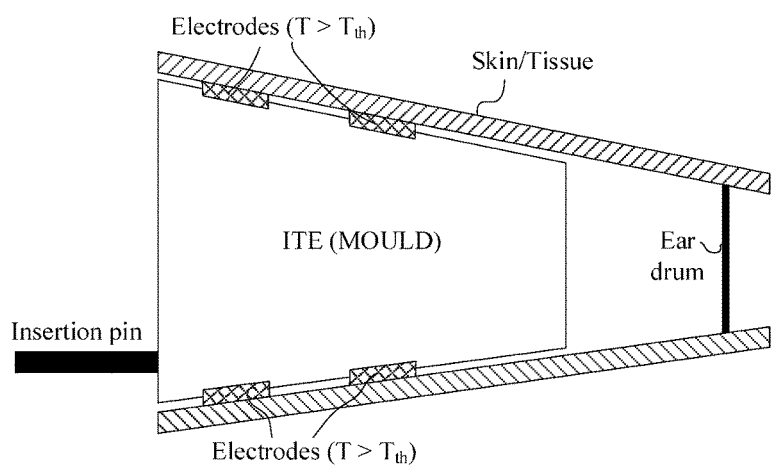

FIG. 2B illustrates the ITE-part of FIG. 2A when mounted in an operational location in the ear canal (where the temperature is assumed to be larger than the threshold temperature ($T>T_{th}$)). In this state, the PR-electrode (Electrodes ($T>T_{th}$)) are shown to protrude from the outer surface of the ITE-part. Thereby a good mechanical and electrical contact to the Skin/tissue of the ear canal is provided. In an embodiment, the ITE-part is adapted to be located deep in the ear canal of the user, e.g. fully or partially in the bony part of the ear canal.

Figure 3A:
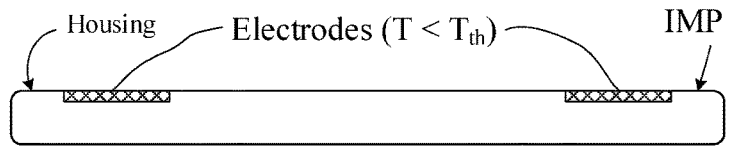
FIG. 3A shows a cross-sectional view at a temperature below a threshold temperature of an implanted part of a cochlear implant hearing device with a housing comprising PR-electrodes for picking up physiological responses, e.g. brainwave signals, from the user
Figure 3B:
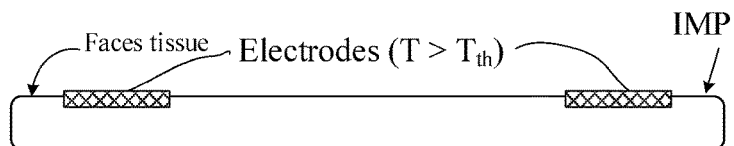
FIG. 3B shows the same cross-sectional view of the implanted part of FIG. 3A, but at a temperature above the threshold temperature.

FIG. 3A shows a cross-sectional view at a temperature below a threshold temperature of an implanted part (IMP) of a cochlear implant type hearing device with a Housing comprising PR-electrodes (Electrodes ($T<T_{th}$)) for picking up physiological responses, e.g. brainwave signals, from a user. The electrodes are flush with the outer surface of the housing of the implanted part (IMP). FIG. 3B shows the same cross-sectional view of the implanted part (IMP) of FIG. 3A, but at a temperature above the threshold temperature ($T_{th}$), where the PR-electrodes (Electrodes ($T>T_{th}$)) are protruding above the outer surface of the housing of the implanted part (IMP).

Figure 3C:
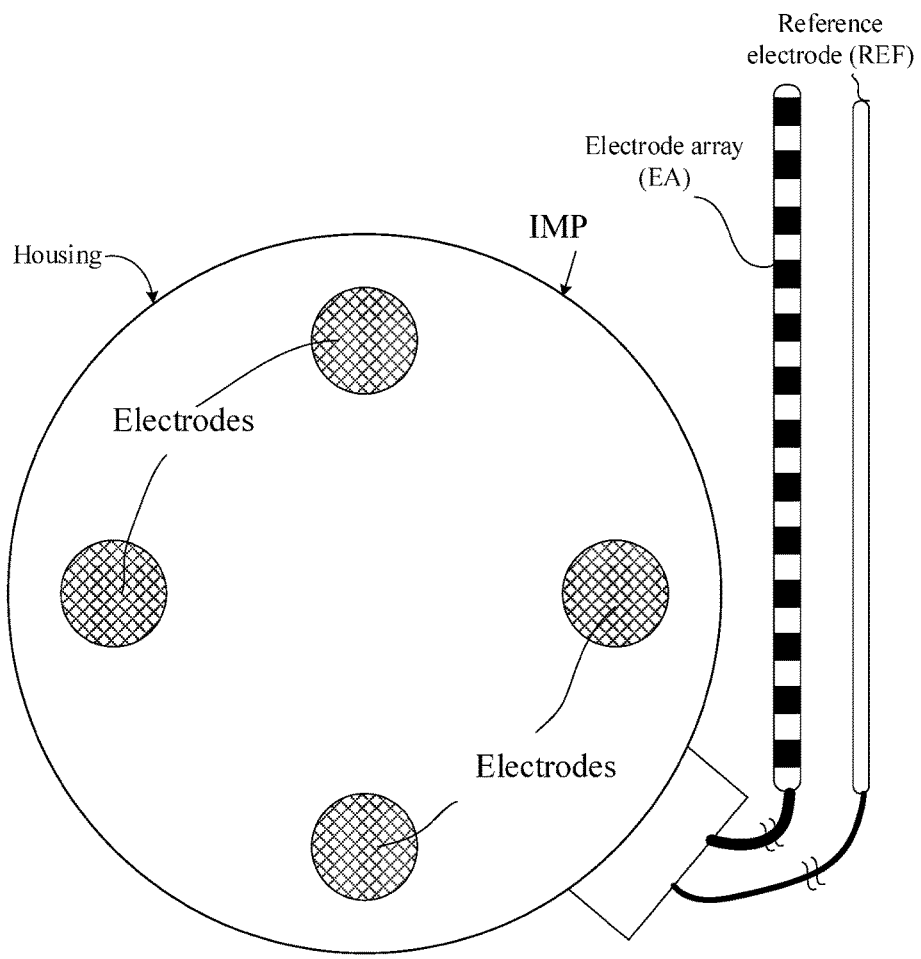
FIG. 3C shows a cross-sectional (skull tissue facing) view of the implanted part perpendicular to the view of FIG. 3A and additionally including an electrode array and a reference electrode electrically connected to electronic components of the implanted part.
Figure 4:
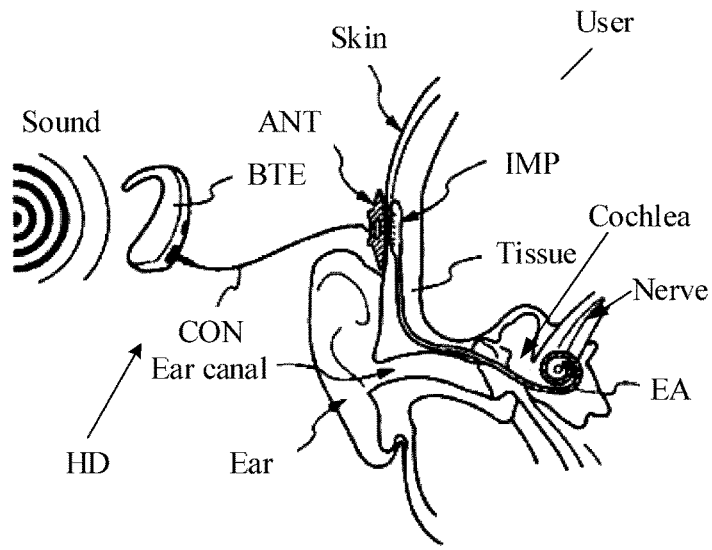
FIG. 4 shows an embodiment of a cochlear implant type hearing device according to the present disclosure comprising an external (processing) BTE-part for picking up sound from the environment and adapted for being located at an ear (pinna) of the user, a further external part for providing communication between the BTE-part and an implanted part connected to an electrode array mounted in cochlea and configured to electrically stimulate the auditory nerve based on sound inputs processed by the BTE-part.

FIG. 3C shows a cross-sectional (skull tissue facing) view of the implanted part perpendicular to the view of FIG. 3A and additionally including an electrode array (EA) and a reference electrode (REF) electrically connected to components of the implanted part. The implanted part IMP comprises an Electrode array (EA) configured to be inserted into cochlea for electrically stimulating (and/or picking up evoked potentials from) the hearing nerve. The implanted part IMP further comprises a Reference electrode (REF) for providing a reference potential for possible (e.g. evoked) potentials picked up by the electrode array and/or for electronic circuits of the implanted part. The Reference electrode may further provide a reference potential for brainwave signals (e.g. EEG- or EOG-signals) picked up by the Electrodes on the Housing of the IMP part. Four PR-electrodes (Electrodes) are shown on the Housing of the implanted part (IMP). Other number of electrodes may be located on the Housing depending on the specific application. In an embodiment, the surface area/perimeter area of the Electrodes is optimized for one or more of the Electrodes. FIG. 4 shows an embodiment of a cochlear implant type hearing device (HD) according to the present disclosure comprising an external (processing) BTE-part (BTE) for picking up Sound from the environment and adapted for being located at an Ear (pinna) of the User. The hearing device comprises a further external part (ANT) comprising antenna and transceiver circuitry for providing communication between the BTE-part (BTE) and an implanted part (IMP) through the Skin of the user. The BTE-part and the further external part (ANT) are electrically connected via a connecting element (CON), which may be an electric cable comprising electric conductors as shown in FIG. 4, or in another embodiment a wireless link. In a further embodiment, the BTE-part (BTE) and the further external part (EXT) are integrated in one part. The implanted part (IMP) is connected to an electrode array (EA) mounted in Cochlea and configured to electrically stimulate the auditory nerve (Nerve) based on sound inputs processed by the BTE-part. The implanted part (IMP) comprises (as shown in FIG. 3A, 3B, 3C) PR-electrodes for picking up (e.g. evoked) potentials from the user's brain on a surface facing Tissue covering the skull of the User.

Figures 5A, 5B:
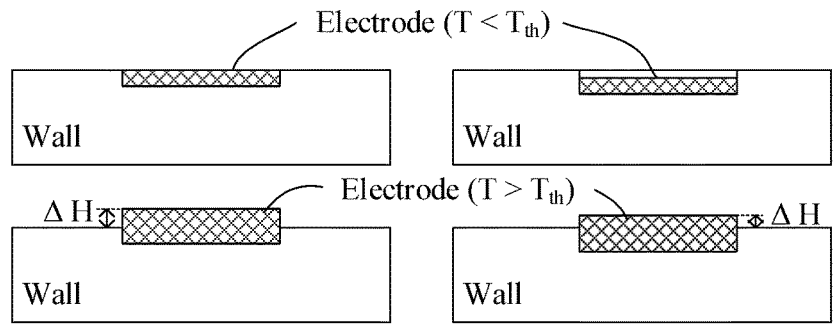
FIG. 5A shows a first embodiment of a PR-electrode unit according to the present disclosure at temperatures below and above a threshold temperature, respectively.
FIG. 5B shows a second embodiment of a PR-electrode unit according to the present disclosure at temperatures below and above a threshold temperature, respectively.

FIG. 5A shows a first embodiment of a PR-electrode unit comprising a PR-electrode (Electrode) according to the present disclosure at temperatures below ($T<T_{th}$) and above ($T>T_{th}$) a threshold temperature ($T_{th}$), respectively. In the embodiment of FIG. 5A, the outer surface of the PR-electrode is flush with the outer surface of the housing (Wall) of the first (external or implanted) part when the temperature is below the threshold temperature ($T_{th}$), cf. upper part of FIG. 5A. When the temperature is above the threshold temperature ($T_{th}$), the outer surface of the PR-electrode is elevated ($\Delta H$) compared to the outer surface of the housing (Wall) of the first part, as illustrated in the lower part of FIG. 5A. The change in elevation of the outer surface of the PR-electrode relative to the outer surface of the housing (Wall) of the first part from 0 to $\Delta H$ is provided by a larger expansion of the material of the PR-electrode in height compared to the material of the housing of the first part. FIG. 5B shows a second embodiment of a PR-electrode unit comprising a PR-electrode (Electrode) according to the present disclosure at temperatures below ($T<T_{th}$) and above ($T>T_{th}$) a threshold temperature ($T_{th}$), respectively. In the embodiment of FIG. 5B, the outer surface of the PR-electrode is depressed in the surface of the housing (Wall) of the first part at temperatures below the threshold temperature ($T_{th}$), and to protrude ($\Delta H$) from the surface when heated to temperatures above the threshold temperature. The change is e.g. achieved as explained in connection with FIG. 5A.

Figure 5C:
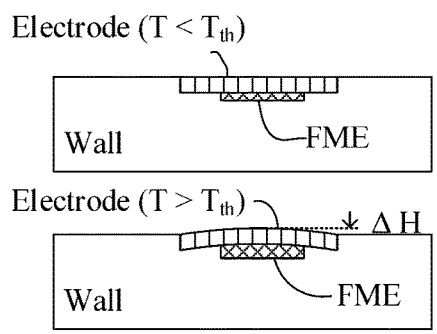
FIG. 5C shows a third embodiment of a PR-electrode unit according to the present disclosure at temperatures below and above a threshold temperature, respectively.

FIG. 5C shows a third embodiment of a PR-electrode unit comprising a PR-electrode according to the present disclosure at temperatures below ($T<T_{th}$) (upper drawing) and above ($T>T_{th}$) (lower drawing) a threshold temperature ($T_{th}$), respectively. As in FIG. 5A, the outer surface of the PR-electrode is flush with the outer surface of the housing (Wall) of the first (external or implanted) part when the temperature is below the threshold temperature ($T_{th}$), and curved above the outer surface of the housing when heated to temperatures above the threshold temperature. The change in relative elevation of the two surfaces is achieved by a form modifying element (FME) located beneath the PR-electrode. In an embodiment, the material of the modifying element (FME) (or the PR-electrode itself) exhibits an anisotropic expansion. In an embodiment, the modifying element (FME) (or the PR-electrode itself) is configured to exhibit a larger expansion in a direction perpendicular to the outer surface of the housing than parallel thereto when heated around the threshold temperature. When heated above the threshold temperature the form modifying element (FME) is configured to expand more in a direction perpendicular to the outer surface of the PR-electrode than the PR-electrode itself, and more than that of the housing to provide an elevation ($\Delta H$) of the PR-electrode relative to housing surface. In an embodiment, the PR-electrode is fixed at its periphery to force the expansion to be predominantly at the center of the electrode surface as illustrated by the curved shape of the electrode in the lower part of FIG. 5C.

The PR-electrode comprises an electrically conductive material, e.g. a metal or metal alloy, such as a shape memory allow. In an embodiment, the PR-electrode comprises Carbon in an electrically conductive form, e.g. in the form of graphite or graphene. In an embodiment, the threshold temperature is in the range from 34° C. to 36° C. In an embodiment, the PR-electrode is configured to have a first shape below the threshold temperature ($T_{th}$) and a second shape above the threshold temperature. In an embodiment, the dimension in one direction (e.g. perpendicular to the outer surface of the electrode) is increased when the temperature is increased from below to above the threshold temperature ($T_{th}$). In an embodiment, the shape of the PR-electrode below the threshold temperature ($T_{th}$) relates to a deformed state. In an embodiment, the shape of the PR-electrode above the threshold temperature ($T_{th}$) relates to a relaxed state. In an embodiment, the outer surface of the PR-electrode is elevated ($\Delta H$), e.g. between 0.5 and 1 mm or ≥1 mm, compared to the outer surface of the housing (Wall) of the first part.

Figure 6:
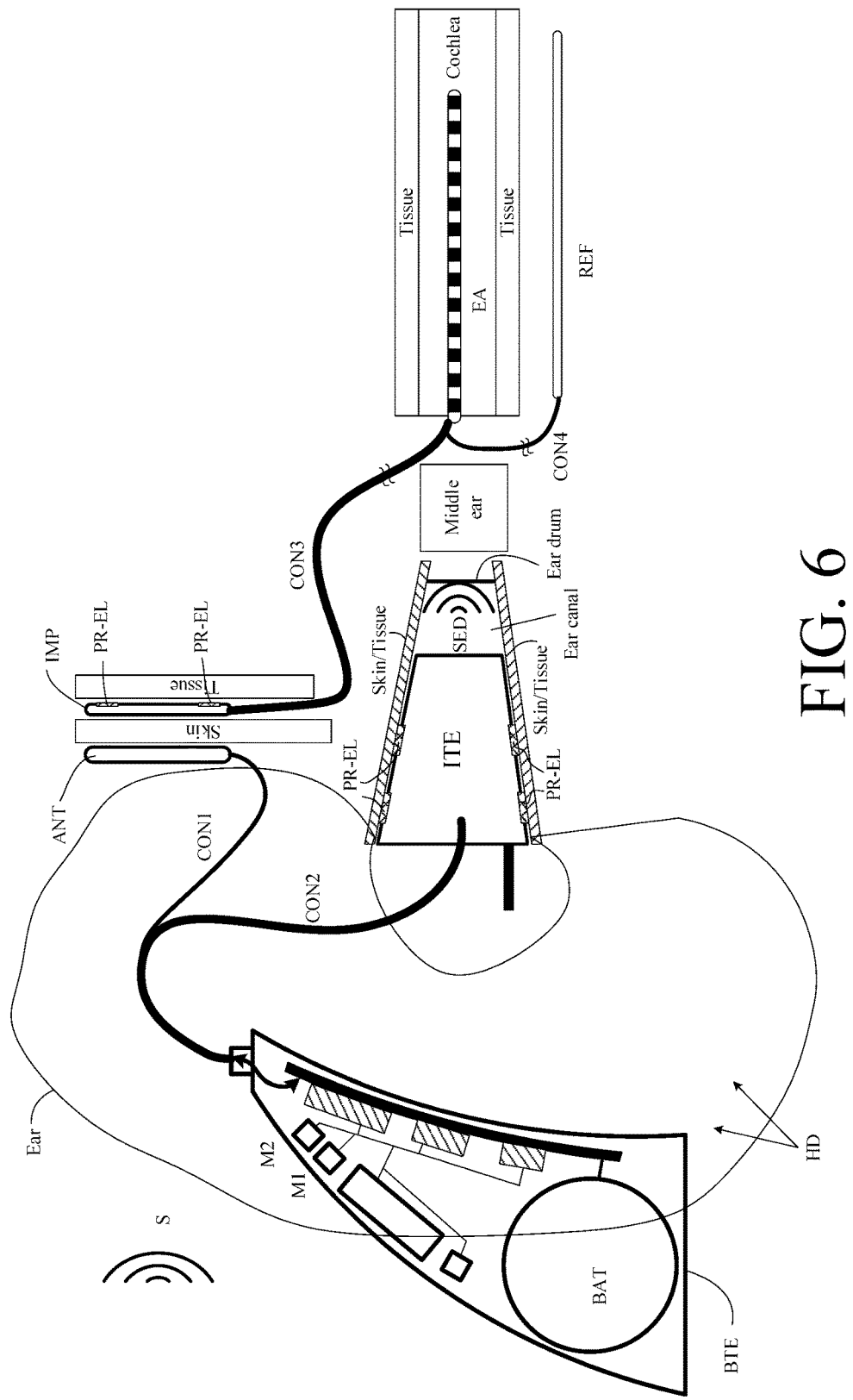
FIG. 6 shows an embodiment of a hybrid hearing device according to the present disclosure comprising an external part for acoustically stimulating an ear of a user and an implanted part for electrically stimulating the auditory nerve of the (same) ear.

FIG. 6 shows an embodiment of a hybrid hearing device (HD) according to the present disclosure comprising an external part (ITE) for acoustically stimulating an ear of a user and an implanted part (IMP) for electrically stimulating the auditory nerve of the (same) ear of the user. The hybrid hearing device comprises a part (ITE) adapted to be inserted into an ear canal of the user to allow acoustic stimulation of the ear drum (Ear drum) from a loudspeaker located in the ITE-part, or in another part of the hearing device in acoustic communication with the ITE-part (e.g. via a tube). The implanted part (IMP) is adapted for being implanted in the head of the user (cf. e.g. FIG. 3A, 3B, 3C). The hearing device (HD) further comprises a BTE-part adapted for being located at the ear (Ear), e.g. behind the ear (BTE), and a further external part (ANT) electrically connected to the BTE-part via a connecting element CON1. The further external part (ANT) comprises antenna (e.g. an inductor coil) and transceiver circuitry for providing communication between the BTE-part (BTE) and the implanted part (IMP) through the skin (Skin) of the user. The BTE-part is further electrically connected to the ITE-part via a connecting element CON2. The implanted part (IMP) comprises antenna (e.g. an inductor coil) and transceiver circuitry allowing a wireless link to be established between the further external part (ANT) and the implanted part (IMP). The implanted part (IMP) is located under the skin of the user appropriately arranged relative to the further external part (ANT) to allow exchange of data between the two parts and to allow energy from the external part to the implanted part to be transferred. The ITE-part (ITE) and the implanted part (IMP) both comprise PR-electrodes (PR-EL) for picking up (e.g. evoked) potentials (e.g. from the brain) from the user via electrical contact to skin and/or tissue (Skin/Tissue) at the ear or in the ear canal of the user and to the skin and/or skull-tissue (Tissue) under the skin of the user, respectively. The implanted part comprises an electrode array (EA) and a reference electrode (REF) electrically connected to the implanted part (IMP) via electrical connections CON3 and CON4, respectively (e.g. electrical conductors). The reference electrode (REF) is preferably separated from the electrode array (EA) by tissue (Tissue), e.g. in that the electrode array is inserted in cochlea (Cochlea) and the reference electrode is positioned outside cochlea.

In the embodiment of FIG. 6, the ITE-part comprises an electro-acoustic transducer (e.g. a loudspeaker) for acoustically stimulating a first frequency range via sound SED played in the residual volume in front of the ear drum and thereby conveyed to the ear drum and further to cochlea via the middle ear (Middle ear). The first frequency range may be a continuous frequency range between a first lower frequency $f_{as,min}$ and a first upper frequency $f_{as,max}$, or comprise a number of separate frequency ranges between said first upper and lower frequencies. The first lower frequency $f_{as,min}$ may e.g. be at or below 300 Hz, such as below 150 Hz. The first upper frequency $f_{as,max}$ may e.g. be at or below 2 kHz, such as below 1 kHz.

In the embodiment of FIG. 6, the ITE-part comprises an electrode array (EA) for electrically stimulating a second frequency range via separate electric stimuli supplied to at least some of the electrodes of the electrode array when located at the auditory nerve, e.g. in cochlea (Cochlea). The second frequency range may be a continuous frequency range between a second lower frequency $f_{es,min}$ and a second upper frequency $f_{es,max}$, or may comprise a number of separate frequency ranges between said second upper and lower frequencies. The second lower frequency $f_{es,min}$ may e.g. be below 2 kHz, such as below 1 kHz. The second upper frequency $f_{as,max}$ may e.g. be below 8 kHz, such as below 6 kHz.

The first and second frequency ranges may be overlapping or non-overlapping. The first and second frequency ranges may change over time, and be adaptively controlled by the hearing devices, e.g. influenced by physiological responses picked up the PR-electrode units of the external and/or implanted parts.

The hybrid hearing aid (HD) of FIG. 6 thus comprises a receiver in the ear (RITE) type hearing aid and a cochlear implant (CI) type hearing aid. The BTE-part (BTE) adapted for being located behind pinna services the ITE-part as well as the implanted part (IMP) via electrical connections CON2 and CON1, respectively. The BTE part (BTE) comprises two input transducers (here microphones) (M1, M2) each for providing an electric input audio signal representative of an input sound signal from a sound source (S) in the environment of the hearing device. The BTE-part further comprises two wireless receivers (WLR1, WLR2) for providing respective directly received auxiliary audio and/or information signals from other devices. The BTE-part (BTE) further comprises a substrate (SUB) whereon a number of electronic components are mounted, functionally partitioned according to the application in question (analogue, digital, passive components, etc.), but including a configurable signal processing unit (SPU), coupled to each other and to input and output units via electrical conductors Wx. The configurable signal processing unit (SPU) is adapted to provide separate first and second enhanced signals to the ITE-part and to the implanted part (IMP) allowing a separate (simultaneous) acoustic and electric stimulation, respectively, at an ear of the user. The ITE part (ITE) comprises an output unit in the form of a loudspeaker (receiver) for converting the first enhanced signal from the BTE-unit to an acoustic signal comprising frequencies in a first frequency range (providing, or contributing to, acoustic signal SED at the ear drum (Ear drum)). The implanted part (IMP) is configured to generate or convey electric stimuli representative of a second frequency range based on the second enhanced signal from the BTE-unit to the electrode array (EA).

The BTE-part (BTE) further comprises a battery (BAT) for energizing electronic components of the hearing aid (e.g. including electronic components of the ITE-part, the ANT-unit and the implanted part (IMP)).

Figure 7:
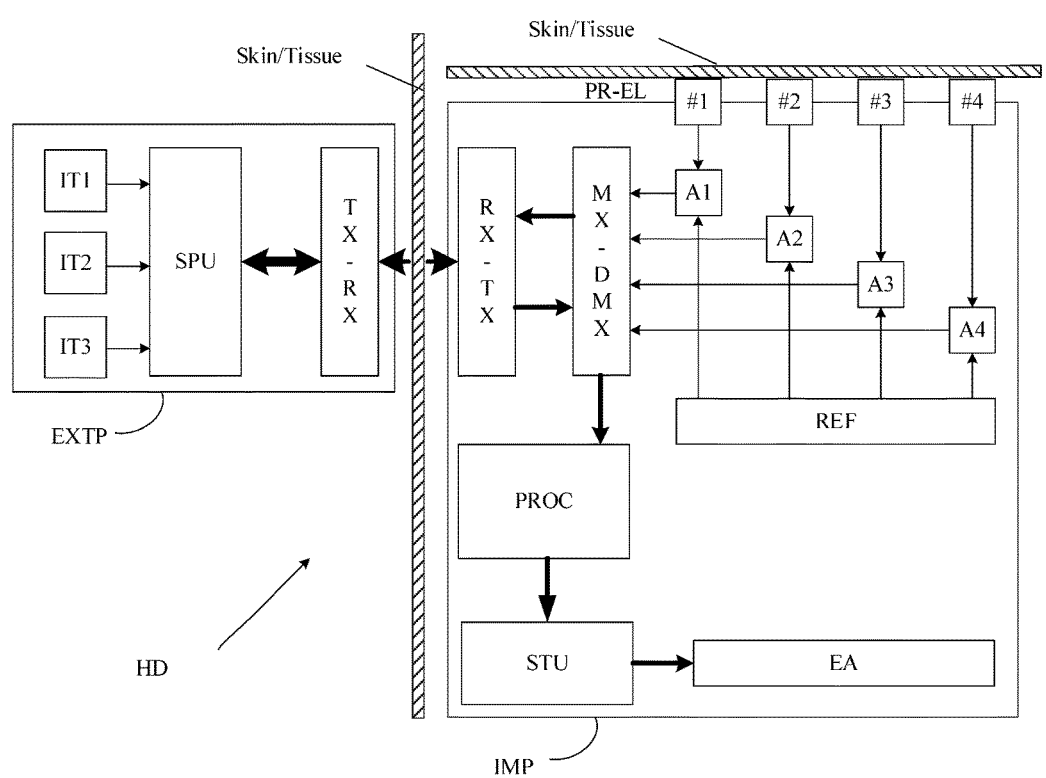
FIG. 7 shows a hearing device according to the present disclosure comprising an external part and an implanted part, the implanted part comprising an electrode array, a reference electrode, and a number of PR-electrode units, where the external as well as the implanted part comprises a processor for controlling and/or influencing the stimulation of electrode array in dependence of signals picked up or received by input units of the external part.

FIG. 7 shows a hearing device (HD) according to the present disclosure comprising an external part (EXTP) and an implanted part (IMP), the implanted part comprising an electrode array (EA), a reference electrode (REF), and a number of PR-electrode units (PR-EL), where the external as well as the implanted part comprises a processor (SPU and PROC, respectively), at least for controlling the stimulation of electrode array (EA). The implanted part comprises a number of PR-electrode units PR-EL #1, #2, #3, #4, and a separate reference electrode (REF). The implanted part (IMP) further comprises a number of amplification units A1, A2, A3, A4 connected to the reference electrode and to a respective one of the PR-electrode units PR-EL #1, #2, #3, #4. The respective amplification units A1, A2, A3, A4 are adapted to provide an amplified voltage difference $\Delta V1$, $\Delta V2$, $\Delta V3$, $\Delta V4$, between the potentials of the respective PR-electrode units and the reference voltage $V_{REF}$. In an embodiment, the amplification units A1, A2, A3, A4 comprise respective analogue-to-digital converters providing the amplified voltage differences $\Delta V1$, $\Delta V2$, $\Delta V3$, $\Delta V4$ as digital signals. Thereby the further processing of the acquired physiologic signals and/or the transmission of the data to another device is/are facilitated. The implanted part (IMP) comprises a multiplexing-de-multiplexing unit (MX-DMX) configured to multiplex the amplified voltage difference $\Delta V1$, $\Delta V2$, $\Delta V3$, $\Delta V4$, and forward them to the processor (SPU) of the external part (EXTP) via the wireless link (TX-RX, RX-TX) between the external (EXTP) and implanted (IMP) parts. The processor (SPU, PROC) is configured to analyse the physiological responses from the PR-electrode units PR-EL #1, #2, #3, #4, and configured to influence or control the stimulation of the hearing nerve by the electrode array based on such analysis. The external part (EXTP) comprises first, second and third input transducers (IT1, IT2, IT3) for picking up sound from the environment and feeding first, second and third electric input signals to the external processor (SPU). The external processor (SPU) is adapted to provide stimuli or data representing electric stimuli to the implanted part (IMP) based on the current electric input signals via the wireless link (TX-RX, RX-TX). The stimuli or data representing electric stimuli are forwarded to the processor (PROC) of the implanted part, either directly or via the multiplexing-de-multiplexing unit (MX-DMX). The processor (SPU, PROC) may further process the stimuli or data representing electric stimuli from the external part, e.g. based on the (e.g. evoked) potentials (or the amplified voltage differences $\Delta V1$, $\Delta V2$, $\Delta V3$, $\Delta V4$) provided by the PR-electrode units PR-EL #1, #2, #3, #4. The possibly further processed stimuli or data representing electric stimuli are fed to the stimulation unit (STU) for application to the individual electrodes of the electrode array (EA).

The hearing device may comprise an external ITE-part located at or in an ear canal in addition to the implanted part, each part comprising one or more PR-electrode units (cf. e.g. FIG. 6). The hearing device may be configured to combine physiological responses picked up the external as well as the implanted PR-electrode units. In an embodiment, the hearing device is configured to use the physiological responses from the PR-electrode units in combination to control processing of the implant. In an embodiment, the hearing device is configured to use the combination of physiological responses to define the distribution of (first and second) frequency ranges (e.g. the minimum and maximum frequencies of the respective frequency ranges) stimulated by the acoustic transducer and the electrode array, respectively.

The hearing device (HD) may e.g. be configured to record an electro oculogram (EOG) for monitoring eye movements of the user.

Among the many possible applications of EEG signals measured in or near the ear canal, Monitoring of epilepsy or epileptic seizure detection is one of the very promising ones. It is known that a very reliable seizure detection can be obtained through data from conventional skull or scalp EEG. Transferring this technology to Ear-level EEG would increase the usefulness of these results due to the portability of Ear-level EEG systems. Such data may also be acquired by invasive ECoG picked up by implanted PR-electrode units, e.g. located in or on the implanted part or picked up by separate (implanted) electrodes. The ECoG may be amplified and processed fully or partially in the implanted part or fully or partially in an external part.

Through the use of electrodes mounted on or integrated into an ear mould or a silicon or TPE dome or similar ear canal interface (e.g. a micro-mould), EEG may be monitored at ear level. This has e.g. been demonstrated in EP2200347B1.

Apart from the audiological applications, a number of health oriented applications exist. Monitoring of diabetes has been described (for instance in US20120238856A1). Epilepsy & seizures have been rather briefly mentioned in EEG patent publications (US20120238856A1, US20030195588A1, US20060094974A1).

Monitoring for epileptic seizures (absence seizures) has been demonstrated to be very reliable (cf. e.g. [Eline B. Petersen et al.; 2011]) based on conventional scalp EEG by means of identification of a characteristic 3 Hz spike-and-wave complex and by means of wavelet transform based methods. These results may be transferred to ear-level EEG.

The hearing device (HD) may e.g. be configured to monitor epilepsy or epileptic seizures based on the physiological responses from said PR-electrode units. In an embodiment, EEG or other evoked potentials, picked up by PR-electrode units of an implanted part of a cochlear implant type hearing device are forwarded to an external processer for analysis. In an embodiment, the data from the PR-electrode units are analysed in a processor of the implanted part, and or on a processor of an external processor forming part of the hearing device.

The present disclosure addresses the challenge of integrating electrodes in an ear mould (or other element introduced into an ear canal of the user) in a way in which comfort for the user is maintained while good robust skin contact and, preferably, ease of manufacture is ensured.

FIG. 8A, 8B, 8C illustrates a micro-mould (cf. Micro-mould in FIG. 8A, 8B, 8C) intended for insertion in an ear canal of user and e.g. used in combination with a receiver-in-the-ear- (RITE) type hearing instrument, i.e. the micro-mould is attached to the speaker module, e.g. by a mechanical "click on" system. The micro-mould may e.g. be made of an acrylic plastic or similar material. It may also be made from a mechanically (partly) flexible material. The micro-mould is e.g. based on an individual ear impression (and/or on individual ear-scans) and manufactured by 3D printing techniques such as SLA or SLS technologies. Typically, the micro-mould does not contain any electronic components.

However, according to a further aspect of the present disclosure, grooves (cf. Grooved for electrodes in FIG. 8A, 8B, 8C) are printed into the micro-mould along the dimension which is parallel to the axis from ear canal entrance to ear drum (when the micro-mould is mounted in the ear canal, cf. Axis, and Towards ear drum in FIG. 8A). These grooves allow for mounting of electrodes (cf. Electrode in FIG. 8B), e.g. made of metal or conducting textile or conducting rubber. The electrodes may also be printed or moulded directly into the groove in a process utilizing two or more different materials, one of which is electrically conducting. In an embodiment, the electrode material is adapted to have an outer surface that is flush with or depressed in the surface of the micro-mould at temperatures below a threshold temperature (e.g. 37°), and to protrude from the surface when heated to temperatures at or above said threshold temperature (to improve electrical contact and mechanical fixation). The considerable physical length of the electrodes ensures a stable electrical contact with the skin in spite of movements in the ear canal.

The placement of the electrodes also ensures the ability to connect to them in a stable and manufacturable way—probably through the face of the micro-mould closest to the ear canal entrance, where the micro-mould is attached to the speaker module.

The grooves for electrodes are shown to be evenly distributed around the perimeter of a cross-section of the micro-mould (e.g. 4 evenly distributed grooves are shown). The placement of the grooves may further be guided by,
 a) A priori knowledge of best EEG measurement positions for obtaining suitable EEG signals addressing a particular need (either related to health monitoring or to the extraction of audiologically relevant information).
 b) As in point a) but determined by individual electrical measurement on the client or hearing aid user in question.
 c) Guided by ear canal geometry analysis data as exemplified by retention points (as e.g. discussed in EP2986031A1).

In an embodiment, a micro-mould is configured to have an extension into the pinna region (e.g. into concha) for increased retention in the ear canal.

In a further aspect, it is proposed to apply electrodes to a soft dome or dome-like guiding element forming part of a hearing aid for being inserted into an ear canal of a user.

Many hearing aid users prefer wearing receiver-in-the-ear- (RITE) type hearing instruments equipped with a soft dome. This is a very comfortable solution, which can help many users—provided that the hearing loss is not too severe.

In future hearing instruments, electrodes, e.g. EEG electrodes, may be relevant in order to enable a variety of applications ranging from audiological features, exemplified by controlling the directionality in the hearing aid by unconscious control through the acquired EEG (or EOG) signals or signal patterns, to general health applications and specific diagnostic applications, such as monitoring for epilepsy or hypoglycemia.

State of the art experimental earEEG electrodes are based on acrylic material moulds on the surface of which conductive (metallic) areas are mounted. A dome-type solution would be very comfortable and is expected to fulfil the needs of many users. Three different realization principles for domes with EEG electrodes are shown in FIG. 9A, 9B, 9C, 9D, 9E.

Figure 9A:
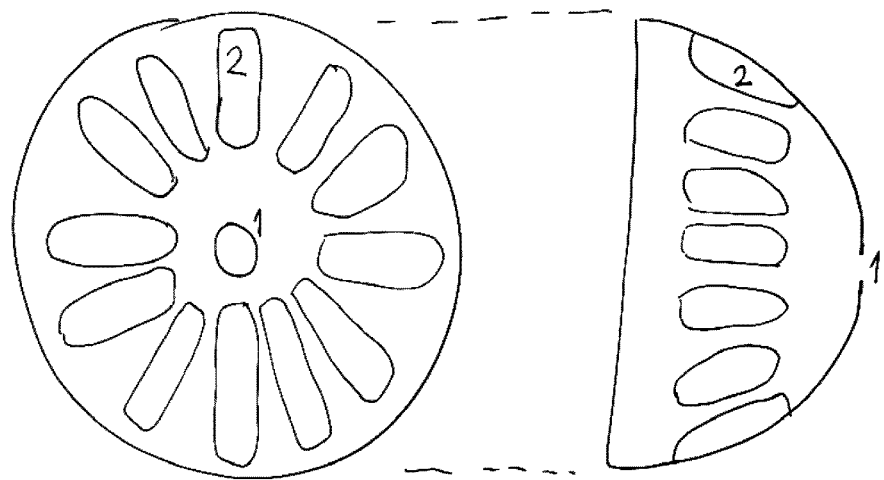
FIGS. 9A, 9B, 9C, 9D, and 9E illustrate aspects of three different realization principles for domes comprising electrodes.

FIG. 9A illustrates a closed dome with 12 electrodes. The electrodes may be used as 12 separate electrodes, or they may be connected in different configurations resulting in a reduced number of electrical terminals. Reference numeral 1 denotes the sound opening, and 2 denotes the (here 12) electrode areas on the surface of the dome.

Figure 9B:
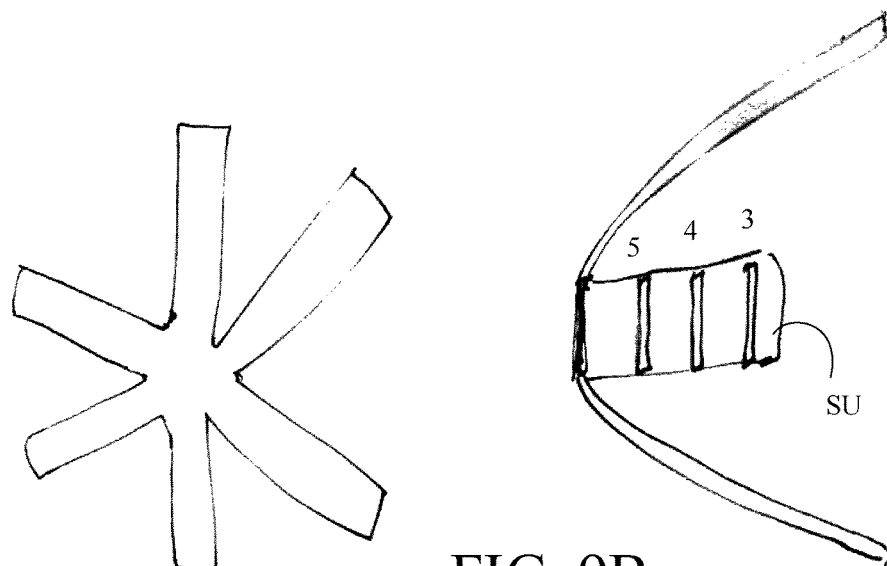
Figure 9C:
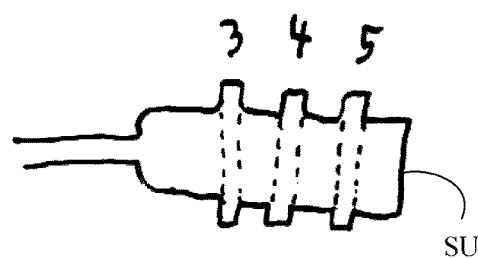

FIG. 9B illustrates an open dome. Each electrode has its own "leg" as illustrated in the left part of FIG. 9B. The right part of FIG. 9B shows a cut-through with rings allowing for connection between dome electrodes and speaker unit (SU) contact areas (3, 4, 5). FIG. 9C illustrates a more detailed view of the possibility for connecting dome electrodes with (e.g. protruding) contact rings on the outer surface of the speaker unit (SU). In FIGS. 9B and 9C, three electrical connections are indicated (by reference numerals 3, 4 and 5).

Figure 9D:
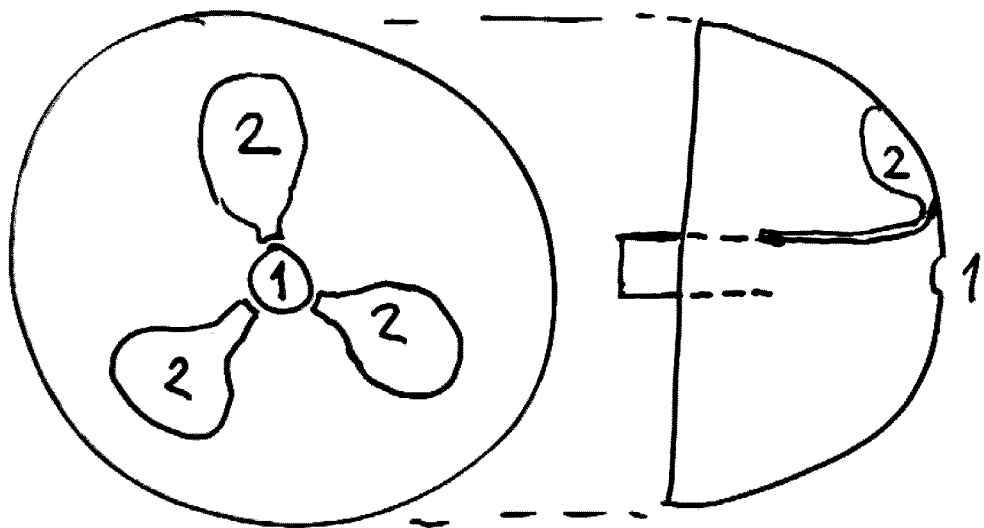
Figure 9E:
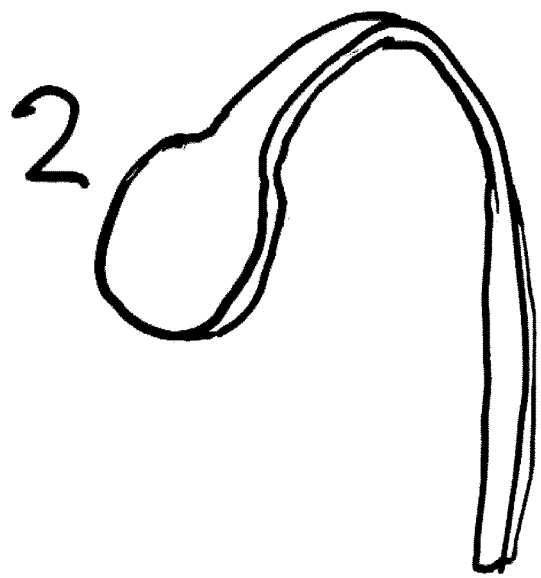

FIG. 9D illustrates a dome with sound opening (1) and three electrodes (2), e.g. EEG electrodes, which may be made from metal or conductive rubber moulded together with a soft non-conducting material such as TPE or silicone. FIG. 9E shows details of one of the electrodes (2) of the embodiment of FIG. 9D—shaped like "a flower". The electrode may e.g. be fabricated from gold, silver or conductive rubber.

Figure 10A:
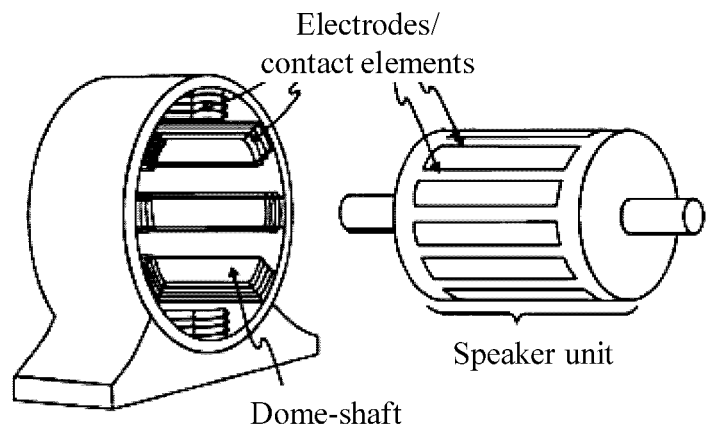
FIG. 10A, 10B illustrate an embodiment of the placement of electrodes and contact elements located on the dome and a speaker casing, respectively, in a "rotor-stator"-like configuration.
Figure 10B:
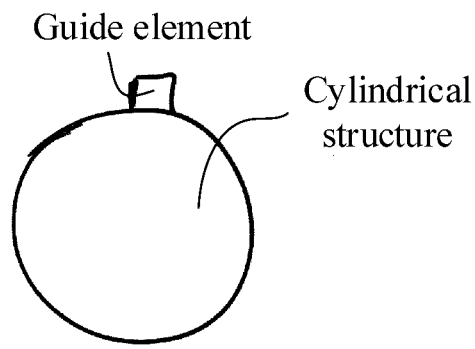

In relation to the electrical connection between a dome with EEG terminals and the electrical terminals on the speaker unit, the principle from FIG. 9C may be applied, in which each ring represents (or is connected to) one terminal. Alternatively, one ring may be subdivided into a number of angular segments, each representing one electrical terminal (like a rotor-stator principle of an electro motor). FIG. 10A shows the basic principle of the placement of the electrodes and contact elements located on the dome (Dome-shaft) and speaker casing (Speaker unit), respectively, where the part resembling a "stator" represents the dome-shaft and the part resembling a "rotor" represents the equivalent of the speaker unit contacts (cf. respective items denoted Electrodes and contact elements, respectively, in FIG. 10A). FIG. 10B shows a Cylindrical structure with simple mechanical guide element (Guide element) shaped as a protrusion along the Cylindrical structure. This structure should be matched with an equivalent shape in the opposite matching part (e.g. the structure denoted Dome-shaft in FIG. 10A).

The electrodes described in relation to the above sketches may be used as passive electrodes (meaning that the electrical amplification, impedance matching and analogue to digital conversion, etc., is done in the hearing instrument body), or as active electrodes (meaning that all or some of the aforementioned processing is performed in close proximity to the electrodes). For the active electrodes the processing may be done in the speaker unit and in this way the number of electrical connections necessary between hearing instrument body and speaker unit may be limited.

The hearing device (HD) may e.g. comprise a hearing aid for compensating a user's hearing impairment.

The signals, e.g. evoked potentials, picked up by the PR-electrode units of the implanted part and/or of the external part may be used to determine whether or not a given electrode of the electrode array (EA) functions and/or whether the stimulation of a given electrode of the array results in an evoked response by analysis of the amplified voltage differences ($\Delta V1$, $\Delta V2$, $\Delta V3$, $\Delta V4$) provided by the PR-electrode (and amplification) units in relation to the applied stimuli.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more. Accordingly, the scope should be judged in terms of the claims that follow.

NON-PATENT LITERATURE

[Eline B. Petersen et al.; 2011] Eline B. Petersen, Jonas Duun-Henriksen, Andrea Mazzaretto, Troels W. Kjar, Carsten E. Thomsen, and Helge B. D. Sorensen, *Generic Single-Channel Detection of Absence Seizures*, 33$^{rd}$ Annual International Conference of the IEEE EMBS, Boston, Mass. USA, Aug. 30-Sep. 3, 2011, pp. 4820-4823.

The invention claimed is:

1. A hearing device comprising
a first part for being inserted in an ear canal or fully or partially implanted in the head of a user, the first part comprising at least one electrode unit, termed a PR-electrode unit, for making contact to skin or tissue of a user when mounted or implanted in an operational condition, the at least one PR-electrode unit being configured to pick up a physiological response from the user; and
a housing and/or a guiding element, wherein
the at least one PR-electrode unit comprises an electrode comprising an electrically conductive material, and
the at least one PR-electrode unit comprises a PR-electrode that is adapted to have an outer surface that is flush with or depressed in the surface of the housing and/or guiding element of the first part at temperatures below a threshold temperature, and to protrude from the surface when heated to temperatures at or above said threshold temperature.

2. A hearing device according to claim 1 wherein the PR-electrode unit comprises a shape-memory material.

3. A hearing device according to claim 1 configured to provide that said threshold temperature is below a normal body temperature of a human being.

4. A hearing device according to claim 1 configured to provide that said threshold temperature is below 37° C.

5. A hearing device according to claim 1 wherein the first part comprises a part for being inserted in an ear canal of the user.

6. A hearing device according to claim 1 wherein the first part comprises a part for being fully or partially implanted in the head of the user.

7. A hearing device according to claim 6 comprising an electrode array for electrically stimulating a hearing nerve of the user, and a processor for analysing the physiological responses from the PR-electrode units, and configured to influence or control the stimulation of the hearing nerve based on such analysis.

8. A hearing device according to claim 1 comprising a separate reference electrode implanted in the head of the user.

9. A hearing device according to claims 1 comprising an external ITE-part located at or in an ear canal and an implanted part, each part comprising one or more PR-electrode units, the hearing device being configured to combine physiological responses picked up said PR-electrode units.

10. A hearing device according to claim 9 wherein said external ITE-part comprises an electro-acoustic transducer for acoustically stimulating a first frequency range and wherein said implanted part comprises an electrode array for electrically stimulating a second frequency range.

11. A hearing device according to claim 9 configured to use the physiological responses from said PR-electrode units in combination to control processing of the implanted part.

12. A hearing device according to claim 1 configured to record an electro oculogram (EOG) for monitoring eye movements of the user.

13. A hearing device according to claim 1 configured to monitor epilepsy or epileptic seizures based on the physiological responses from said PR-electrode units.

14. A hearing device according to claim 1 wherein said at least one PR-electrode is located on a housing or an ear mould or a guiding element of the first part.

15. A hearing device according to claim 14 wherein said guiding element comprises a micro-mould or a dome.

16. A hearing device according to claim 1, wherein the at least one PR-electrode comprises an active electrode in the meaning that at least one of electrical amplification, impedance matching and analogue to digital conversion is performed in close proximity to the electrodes.

17. A hearing device according to claim 1 wherein the first part comprises a housing or an ear mould or a guiding element, wherein one or more grooves are formed into the surface of the housing or ear mould or guiding element along a dimension which is parallel to an axis from ear canal entrance to ear drum when the first part is mounted in the ear canal.

18. A hearing device according to claim 1 comprising a hearing aid for compensating a user's hearing impairment.

19. A binaural hearing system comprising first and second hearing devices according to claim 1, the first and second hearing devices comprising circuitry for establishing a communication link between them to allow the transmission of audio and/or information signals from one to the other.

\* \* \* \* \*